United States Patent
Schreiber et al.

(10) Patent No.: US 6,822,138 B1
(45) Date of Patent: Nov. 23, 2004

(54) NIK-KNOCKOUT MICE

(75) Inventors: Robert D. Schreiber, St. Louis, MO (US); David V. Goeddel, Hillsborough, CA (US); Steven L. Teitelbaum, St. Louis, MO (US); Holger Wesche, San Francisco, CA (US)

(73) Assignee: Washington University in St. Louis, St. Louis, MO (US)

( * ) Notice: Subject to any disclaimer, the term of this patent is extended or adjusted under 35 U.S.C. 154(b) by 121 days.

(21) Appl. No.: 09/706,236

(22) Filed: Nov. 2, 2000

(51) Int. Cl.[7] .................. A01K 67/027; C12N 15/00
(52) U.S. Cl. ........................... 800/18; 800/21
(58) Field of Search ................ 800/18, 21, 22; 435/325

(56) References Cited

PUBLICATIONS

Sigmund, Viewpoint: Are studies in genetically altered mice out of control?, 2000, Arterioscler Thromb. Vasc. Biol., vol. 20, pp. 1425–1429.*

Campbell et al., Totipotency or multipotentiality of cultured cells: Applications and progress, 1997, Theriogenology, vol. 47, pp. 63–72.*

Bradley et al., Modifying the mouse: Design and desire, 1992, Bio/Technology, vol. 10, pp. 534–539.*

Wall, Transgenic livestock: Progress and prospects for the future, 1996, Theriogenology, vol. 45, pp. 57–68.*

Mullins, Perspective series: Molecular medicine in genetically engineered animals, 1996, J. Clin. Invest., vol. 97, pp. 1557–1559.*

* cited by examiner

*Primary Examiner*—Anne-Marie Falk
*Assistant Examiner*—Celine Qian
(74) *Attorney, Agent, or Firm*—Townsend and Townsend and Crew LLP

(57) ABSTRACT

The present invention provides transgenic non-human mammals and cells having one or more structurally and functionally disrupted NIK alleles. In addition, the present invention provides methods for making such transgenic mammals and cells, and methods for determining the effect of a compound on an animal or cell that lacks NIK function. The present invention also provides methods for identifying compounds useful in the inhibition of osteoclastogenesis in a mammal, for example to treat osteoporosis or other conditions. Also provided are methods of modulating the extent of osteoclastogenesis in a cell or a mammal using NIK modulators.

7 Claims, 6 Drawing Sheets

A

Targeting construct

Endogenous locus

Targeted locus

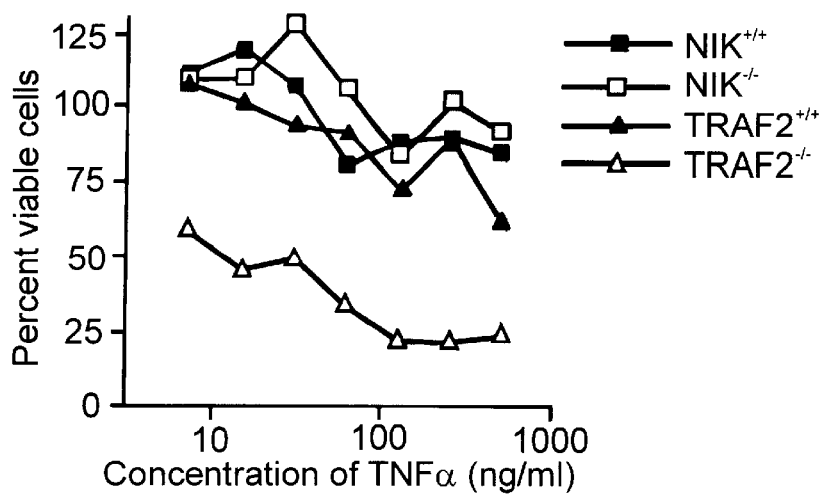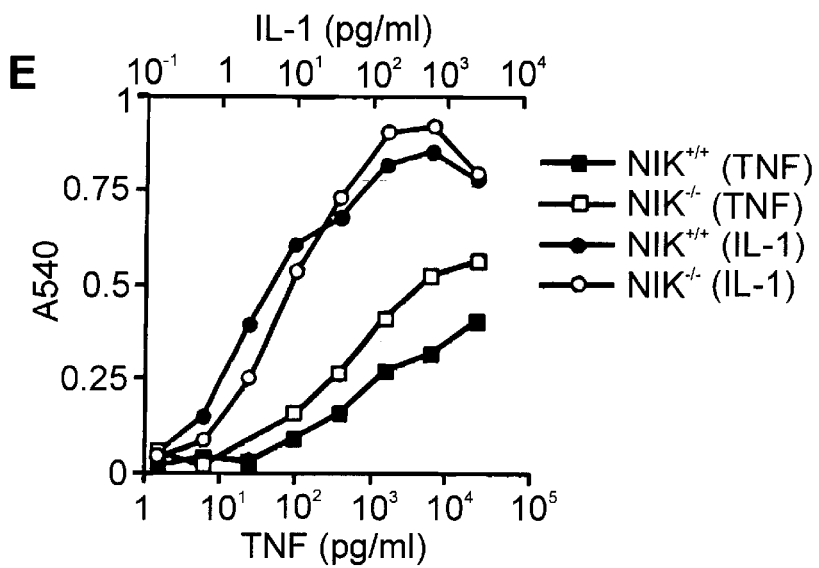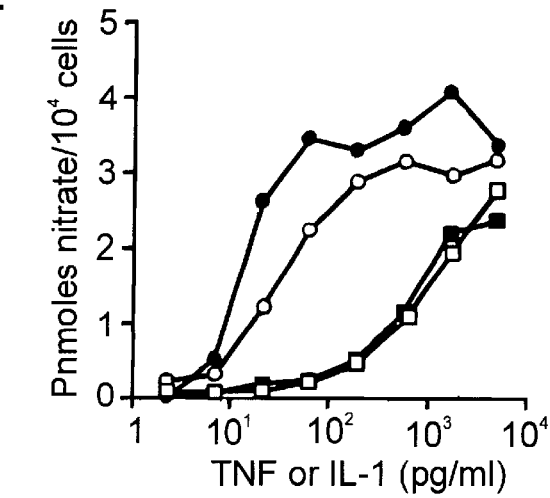

NIK-KNOCKOUT MICE

BACKGROUND OF THE INVENTION

NF-κB is a transcription factor that plays a critical role in promoting immunologic and proinflammatory responses. NF-κB can be activated by a variety of cell surface receptors including members of the TNF receptor family and the Toll-like receptor (TLR) family (Ghosh, S., et al. (1998) *Annu. Rev. Immunol.*, 16:225). Although different receptors often employ distinct combinations of intracellular adapter proteins to initiate the NF-κB activation process, the signals converge downstream into a common pathway that leads to phosphorylation and degradation of the NF-κB inhibitory protein IκB. The precise step where signal integration occurs remains unclear (Ghosh, S., et al. (1998) *Annu. Rev. Immunol.*, 16:225; Karin, M., (1999) *J. Biol. Chem.*, 274:27339).

One element common to many NF-κB activation pathways is the IκB kinase (IKK) complex, a cytokine-activated, multicomponent complex that specifically phosphorylates IκB on two serine residues. The IKK complex consists of two kinase subunits (IKKα and IKKβ) and one regulatory subunit (NEMO or IKKγ) and is thought to be activated by phosphorylation of activation loop serines in IKKα and IKKβ (Regnier, C., et al. (1997) *Cell*, 90:373; DiDonato, J., et al. (1997) *Nature*, 388:548; Mercurio, F., et al. (1997) *Science*, 278:860; Woronicz, J., et al. (1997) *Science*, 278:866; Zandi, E., et al. (1997) *Cell*, 91:243; Yamaoka, S., et al. (1998) *Cell*, 93:1231; Rothwarf, D., et al. (1998) *Nature*, 395:297).

NIK (NF-κB inducing kinase), a MAP3K-like kinase, has been reported to be the kinase responsible for IκB activation by many different stimuli (Malinin, N., et al. (1997) *Nature*, 385:540; Song, H., et al. (1997) *Proc. Natl. Acad. Sci. U.S.A.*, 94:9792). A role for NIK in the NF-κB signaling pathway has been inferred based on various observations, including that overexpression of NIK induces NF-κB activation in cells in a ligand-independent manner and that overexpression of a kinase inactive, NIK mutant inhibits NF-κB activation by a variety of ligands (Malinin, N., et al. (1997) *Nature*, 385:540; Song, H., et al. (1997) *Proc. Natl. Acad Sci. U.S.A.*, 94:9792).

Recently a mutant strain of mice (alymphoplasia mice, aly/aly mice) has been identified that produce a mutant form of NIK. The abnormal protein is catalytically active but contains a single amino acid substitution near the carboxyterminus in a region that can interact with the TRAF family of adapter proteins (Shinkura, R., et al. (1999) *Nat. Genet.*, 22:74). These mice display defective lymph node (LN) development, lack IgA and have significantly reduced serum levels of IgM and IgG (Miyawaki, S., et al. (1994) *Eur. J. Immunol.*, 24:429). Embryonic fibroblasts (MEFs) derived from these mice activate normal levels of NF-κB in response to TNF, and the mice show unaltered LPS-induced shock responses (Shinkura, R., et al. (1999) *Nat. Genet.*, 22:74). However, due to the presence of a catalytically-active mutant NIK protein in the aly/aly mouse, it is not possible to draw firm conclusions based on these findings about the role of NIK in either NF-κB signaling or induction of cytokine-dependent biologic responses.

The integrity of the skeleton is maintained by a balance between osteoclasts, which promote bone resorption, and osteoblasts, which promote bone production. Under some circumstances, such as with age or under certain medical conditions, the balance of bone resorption and rebuilding can be disrupted, and bone density can be altered, often having deleterious effects. For example, a loss of bone density can result in conditions such as osteoporosis, which is characterized by low bone mass and structural deterioration of bone tissue, resulting in bone fragility and an increased susceptibility to fractures. In the U.S. today, 10 million individuals are affected by osteoporosis, and an additional 18 million more have low bone mass.

Clearly, there is a need in the art for better tools with which to study the signal transduction pathway leading to NF-κB activation in different cell types. In addition, there is a great need for new methods for treating and preventing osteoporosis and other disorders, such as by inhibiting the activity of osteoclasts. The present invention addresses these and other needs.

SUMMARY OF THE INVENTION

The present invention provides transgenic non-human mammals and cells having one or more structurally and functionally-disrupted NIK alleles. In addition, the present invention provides methods for making such transgenic mammals and cells, as well as methods for determining the effect of a compound on an animal or cell that lacks NIK function. The present invention also provides methods for identifying compounds useful in the inhibition of osteoclastogenesis in a mammal, for example to treat osteoporosis or other conditions. Also provided are methods of modulating the extent of osteoclastogenesis in a cell or a mammal using NIK modulators.

In one aspect, therefore, the present invention provides a transgenic non-human mammal having at least one structurally and functionally disrupted NIK allele, wherein said NIK allele is disrupted by insertion of a transgene within a NIK locus within the genome of said mammal.

In one embodiment, the mammal is homozygous for the disrupted NIK allele. In another embodiment, the mammal shows one or more phenotypic effects of the disrupted NIK allele selected from the group consisting of impaired lymph node development, absence of Peyer's Patches, disrupted lymphoid architecture, decreased IgA levels, decreased IgG2b levels, impaired NF-κB activation in response to anti-LTβR and impaired osteoclastogenesis in response to OPGL. In another embodiment, the transgene is inserted into the NIK locus by homologous recombination, and the insertion removes at least a portion of an endogenous NIK gene within the genome of said mammal, the portion comprising at least I kb, and including at least 40 codons, of the endogenous NIK gene. In another embodiment, the insertion of the transgene results in the replacement of a portion of the endogenous NIK gene with a nucleic acid sequence encoding a selectable marker. In another embodiment, the selectable marker is a neomycin-resistance gene. In another embodiment, the mammal is a mouse.

In another aspect, the present invention provides a cell derived from any of the above-described transgenic mammals.

In another aspect, the present invention provides an animal model for determining the effect of a test agent on a host deficient in NIK function, the model comprising any of the above-described transgenic mammals.

In another aspect, the present invention provides a method of making a transgenic non-human animal comprising at least one structurally and functionally disrupted NIK allele, the method comprising: (i) transfecting a plurality of embryonic stem cells with a nucleic acid comprising a NIK gene that is disrupted by insertion of a selectable marker, (ii)

selecting for transgenic embryonic stem cells that have incorporated the nucleic acid into their genome; (iii) introducing at least one of the transgenic embryonic stem cells into an embryo to produce a chimeric mammal comprising at least one of the transgenic embryonic stem cells; and (iv) breeding the chimeric mammal with a wild type mammal to obtain F1 progeny that are heterozygous for the disrupted NIK gene.

In one embodiment, the animal is a mouse.

In another embodiment, the present invention provides a method for determining the effect of a test agent on a mammal deficient in NIK function, the method comprising: (i) contacting a transgenic non-human mammal having at least one disrupted NIK allele with said test agent; and (ii) detecting the presence or absence of a functional effect of the test agent in the mammal.

In one embodiment, the mammal is a mouse. In another embodiment, the mammal is homozygous for a structurally and functionally disrupted NIK allele. In another embodiment, the transgenic non-human mammal is generated using any of the abovedescribed methods.

In another aspect, the present invention provides a method of identifying a compound useful in the treatment of osteoporosis in a mammal, the method comprising: (i) contacting a NIK polypeptide with a test compound; and (ii) detecting the functional effect of the test compound on the NIK polypeptide.

In one embodiment, the functional effect comprises an inhibition of NIK kinase activity. In another embodiment, the NIK polypeptide is present within a cell. In another embodiment, the functional effect comprises detecting osteoclastogenesis of the cell.

In another aspect, the present invention provides a method of inhibiting osteoclastogenesis in a cell, the method comprising contacting the cell with a compound that inhibits the activity or expression of NIK in the cell.

In one embodiment, the compound is an antisense oligonucleotide. In another embodiment, the compound is a small molecule inhibitor of NIK kinase activity, or an inhibitor of NIK interaction with receptor or adaptor proteins in cells. In another embodiment, the cell is present within a mammal, and the compound is administered systemically or locally to the mammal. In another embodiment, the compound is identified using any of the above-described methods.

Figure 1:
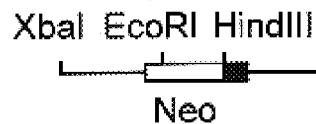
FIG. 1. Targeting of the mouse NIK gene. (A) Map of the NIK targeting vector is shown along with the WT and mutant loci. Exon 1 is represented by a black box and the neomycin resistance gene cassette is indicated by an open box. The probe used for Southern blot analysis is shown as a solid line together with the expected hybridization fragment size. The PCR primers used for screening the mutant allele are shown as arrows. (B) Southern blotting of genomic DNA isolated from the tails of $NIK^{+/+}$, $NIK^{+/-}$, and $NIK^{-/-}$ mice. (C) Expression of NIK protein in cells of the indicated genotypes. Cell lysates were immunoprecipitated with antibodies specific for NIK (top panel) or NEMO (bottom panel) and immunoblotted with anti-NIK or a mixture of anti-IKKα and IKKβ respectively.
Figure 1:
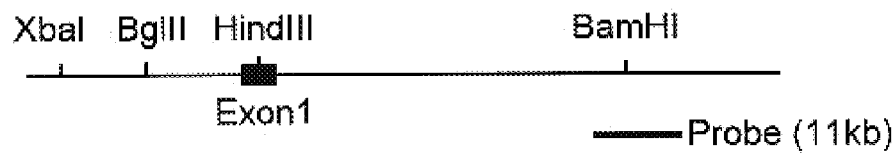
Figure 1:
Figure 1:
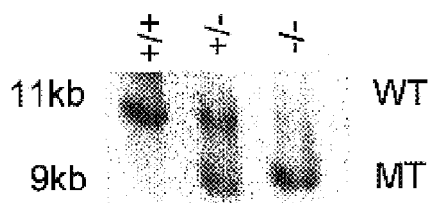
Figure 1:
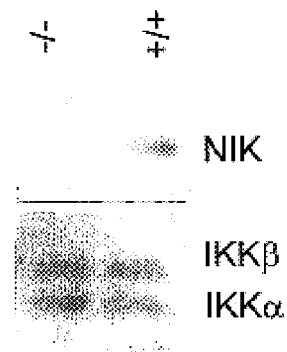

(B) Osteoclastogenesis in vitro was monitored using BMM ($10^6$/ml) cultured in the presence of M-CSF (30 ng/ml) and OPGL (100 ng/ml) for 5–7 days as described (Abu-Amer, Y., et al. (1998) *J. Biol. Chem.*, 273:29417). At the end of the incubation period, cells were fixed and stained for the phenotypic marker tartrate resistant acid phosphatase (TRAP) (Sigma, St. Louis Mo.).

DESCRIPTION OF THE SPECIFIC EMBODIMENTS

I. Introduction

The present invention provides non-human mammals and cells lacking one or more functional NIK alleles, as well as methods for, e.g., making such animals and cells, for using such animals and cells to study NIK function in vivo, and for evaluating side effects of NIK inhibiting compounds. In addition, the present invention provides methods for inhibiting osteoclastogenesis in a cell, methods for treating or preventing various disorders and conditions such as osteoporosis in any mammal including humans, and methods for identifying compounds useful in the treatment of such disorders and conditions.

The transgenic mammals of this invention can be any mammal other than humans. In a preferred embodiment, the mammal is a mouse. Such mammals can be either male or female, and can be either heterozygous or homozygous for the disrupted allele.

The disrupted NIK allele can be completely or partially disrupted. For example, in numerous embodiments, enough of the endogenous gene is removed or interrupted so as to effectively eliminate function of the gene. Such embodiments include, e.g., transgenes that remove or interrupt all or a substantial part of the coding sequence of the NIK gene, or all or a substantial part of a regulatory sequence such as a promoter from a NIK gene, thereby preventing the expression of any functional NIK protein. In other embodiments, a transgene causes a reduction in the function of the NIK gene, for example by reducing expression levels or by introducing a mutation or small deletion into the NIK coding sequence. In other embodiments, a transgene comprising a modified NIK gene is used to replace the endogenous NIK gene, thereby introducing an altered NIK gene with, e.g., enhanced activity, altered biochemical properties, enhanced expression levels, comprising a fusion protein with a heterologous sequence, etc. In another embodiment, the coding sequence of NIK is replaced with a heterologous coding sequence that codes for, e.g., a marker protein such as GFP, β-galactosidase, CAT, etc., allowing the study of NIK regulatory sequences.

The ability of any of the herein-described transgenes to disrupt NIK function can be easily assessed using any of a number of assays, for example by monitoring NIK expression using NIK specific probes or antibodies, as well as by monitoring NIK activity, as detected by, e.g., specific binding assays (e.g., to TRAF1, 2, 3, 5, or 6, to IKK-α or β, or to IκB) or transcription assays (e.g., expression of NFκB-regulated targets). Further, any of a number of physiological assays can be used to detect NIK activity, e.g., osteoclastogenesis, as described infra.

The present transgenic mammals and cells can be used for any of a number of applications. For example, the transgenic mammals, and cells thereof, can be used to assess the functional effect of a test compound on cells or animals lacking NIK. Such methods are usefull to study the effect of an absence or reduction of NIK in a cell, and also to evaluate the side effects that may be caused by a NIK-inhibiting compound. For example, if a compound known to inhibit NIK is administered to a NIK knockout mouse, any detected effects of the compound on the mouse can be concluded to be NIK-independent. Such assays are useful not only to evaluate the precise role of NIK in an animal or a cell, but also to evaluate potential complications associated with a candidate NIK-inhibiting drug. When any of the present assays are performed using cells, the assays are preferably performed in a high-throughput format.

The present invention also provides methods for identifying compounds useful in the treatment of osteoporosis and other NIK-related disorders and conditions. Because the loss of NIK activity results in a decrease in osteoclastogenesis, modulators of NIK can be used to modulate the extent of osteoclastogenesis, in vitro or in vivo. Such modulators are useful for in vitro assays, e.g., to study osteoclastogenesis, as well as for the treatment of bone related disorders and conditions in vivo, e.g., osteoporosis. Because, in addition to osteoclastogenesis, NIK is also involved in a number of other processes, e.g., lymph node development, presence of Peyer's Patches, lymphoid architecture, IgA levels, IgG2b levels, NF-κB activation in response to various stimuli, and others, such compounds are also useful in the treatment or prevention of any disease or condition accociated with any of these processes. For example, any of a large number of immunological diseases, conditions, or processes, e.g., inflammation, can be treated, prevented, or modulated using such compounds.

In addition, the present invention provides methods for the treatment and prevention of any of a number of NIK-related disorders. Any disease or condition can be treated or prevented whose appearance, progression, or severity is related to any of the processes affected by NIK, e.g., lymph node development, presence of Peyer's Patches, lymphoid architecture, IgA levels, IgG2b levels, NF-κB activation in response to various stimuli, and osteoclastogenesis.

II. Definitions

As used herein, the following terms have the meanings ascribed to them below unless specified otherwise.

As used herein, "NIK" refers to a protein kinase, or to a nucleic acid encoding the kinase, as described, e.g., in Malinin et al. (1997) Nature, 385:540–544; Song et al. (1997) PNAS, 94:9792–9796; U.S. Pat. Nos. 5,843,721, 5,844,073, or 5,854,003), or as shown in, e.g., Gendank Accession Nos. NM_016896, AF143094, NM_003954, Y10256, AR068515, AR063065, AR062290, and others, or as isolatable, e.g., from a cDNA or genomic library, from any mammal using probes or primers (see, e.g., SEQ ID NOs: 1–3) derived from any these sequences, or to any derivatives, homologs, mutants, or fragments of any of these sequences.

Topologically, full-length NIK polypeptides include a number of functional domains, including, but not limited to, a serine/threonine protein kinase motif, a kinase domain, a proline rich region, a lysine-rich region, protein binding domains (i.e., domains required for the binding of NIK to heterologous proteins, etc. These domains can be structurally or functionally identified using methods known to those of skill in the art, such as standard sequence analysis programs, by comparison with related proteins, and by in vitro or in vivo assays using, e.g., deleted or mutated forms of NIK.

A "gene" refers to the smallest, independently functional unit of genetic material that can code for and drive the expression of a protein, e.g., NIK, or whose presence or absence has a phenotypic consequence on a cell or organism. An "endogenous gene" refers to a naturally occurring gene, e.g., a NIK gene, as found in a normal, non-mutant individual, and as found in its natural genomic location.

A "transgene" refers to genetic material that is introduced, or is capable of being introduced, into cells of a host animal. Typically, once a "transgene" is introduced into the cells of the host animal, it is maintained, either transiently or permanently, by, e.g., insertion into the host genome. In preferred embodiments of the present invention, a transgene is inserted into the host genome by homologous recombination, thereby replacing the endogenous gene with the transgene. Often, a transgene contains a coding sequence, operably linked to a promoter, that encodes a protein, e.g., a marker protein that allows the detection of the transgene in the cell. "Transgenic" refers to any cell or organism that comprises a transgene.

A "host" animal or mammal refers to any animal that is used to practice the herein-described methods, i.e. animals into which a transgene is introduced to disrupt an endogenous NIK gene. For use in the present invention, such animals include any non-human mammals including, but not limited to, mice, rats, rabbits, and hamsters.

"Biological sample," as used herein, refers to a sample of biological tissue or fluid that contains one or more NIK nucleic acids encoding one or more NIK proteins. Biological samples may also include sections of tissues such as frozen sections taken for histological purposes. A biological sample is typically obtained from any animal, preferably a mammal such as rat, mouse, cow, dog, guinea pig, or rabbit.

By "determining the functional effect" is meant assaying for a compound that modulates, e.g., increases or decreases, a parameter that is indirectly or directly under the influence of NIK, or the NIK pathway, e.g., functional, physical physiological, and chemical effects. Such functional effects can be measured by any means known to those skilled in the art, e.g., changes in spectroscopic characteristics of NIK or any NIK associated molecules (e.g., fluorescence, absorbance, refractive index), hydrodynamic (e.g., shape), chromatographic, or solubility properties, changes in gene expression or activity of NIK, NFκB, or of any marker gene or protein indicative of NIK activity, responsiveness to molecules such as IL-1 or TNF, physiological effects such as osteoclastogenesis, or any other detectable effect on the cell or animal.

"Inhibitors," "activators," and "modulators" of NIK genes or proteins are used interchangeably to refer to inhibiting, activating, or modulating molecules identified using in vitro and in vivo assays for NIK. Inhibitors are compounds that, e.g., bind to NIK proteins, partially or totally block NIK activity, downregulate NIK expression or stability, or prevent NIK binding to heterologous molecules, e.g., TRAF1, 2, 3, 5, or 6, IKK α or β, IκB, etc. Activators are compounds that, e.g., bind to NIK, stimulate NIK activity, increase NIK expression or stability, or facilitate NIK binding to any other protein or factor. Modulators may include genetically modified versions of NIK proteins, e.g., dominant negative or activated forms of NIK. Such assays for inhibitors and activators are described below and include, e.g., providing a NIK-deficient cell or animal, applying putative modulator compounds, and then determining the functional effects of the compound on the cell or animal. Samples or assays comprising the NIK-deficient cell or animal that are treated with a potential activator, inhibitor, or modulator are compared to control samples without the inhibitor, activator, or modulator to examine the effect of the candidate compound Control samples (untreated with the compound) are assigned a relative activity value of 100%. Inhibition of a NIK polypeptide is achieved when the activity value relative to the control is about 80/%, optionally 50% or 25-0%. Activation of a NIK polypeptide is achieved when the activity value relative to the control is 110%, optionally 150%, optionally 200–500%, or 1000–3000% higher.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated NIK nucleic acid is separated from open reading frames that flank the NIK gene and encode proteins other than NIK The term "purified" denotes that a nucleic acid or protein gives rise to essentially one band in an electrophoretic gel. Particularly, it means that the nucleic acid or protein is at least 85% pure, optionally at least 95% pure, and optionally at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Boil. Chem.* 260:2605–2608 (1985); Rossolini et al., *Mol. Cell Probes*, 8:91–98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another.

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, or chemical means. For example, usefull labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementary with the probe sequence depending upon the stringency of the hybridization conditions. The probes are optionally directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 50 amino acids or nucleotides in length, or more preferably over a region that is 75–100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.,* 2:482 (1981), by the homology alignment algorithm of Needleman & Wunsch, *J. Mol Biol.,* 48:443 (1970), by the search for similarity method of Pearson & Lipman, *Proc. Natl. Acad. Sci. U.S.A.,* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment PILEUP uses a simplification of the progressive alignment method of Feng & Doolittle (1987) *J. Mol. Evol.,* 35:351–360. The method used is similar to the method described by Higgins & Sharp (1989) *CABIOS,* 5:151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al. (1984) *Nuc. Acids Res.,* 12:387–395).

Another example of algorithm that is suitable for determining percent sequence identity and sequence similarity are the BLAST and BLAST 2.0 algorithms, which are described in Altschul et al. (1977) *Nuc. Acids Res.,* 25:3389–3402 and Altschul et al. (1990) *J. Mol. Bol.,* 215:403–410, respectively. Software for performing BLAST analyses is publicly available through the National Center for Biotechnology Information (http://www.ncbi.nlm.nib.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences). uses as defaults a wordlength (W) of 11, an expectation (E) or 10, M=5, N=4 and a comparison of both strands. For amino acid sequences, the BLASTP program uses as defaults a wordlength of 3, and expectation (E) of 10, and the BLOSUM62 scoring matrix (see, Henikoff & Henikoff (1989) *Proc. Natl. Acad Sci. U.S.A.,* 89:10915) alignments (B) of 50, expectation (E) of 10, M=5, N=4, and a comparison of both strands.

The BLAST algorithm also performs a statistical analysis of the similarity between two sequences (see, e.g., Karlin &

Altschul (1993) *Proc. Natl. Acad Sci. U.S.A.,* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Such washes can be performed for 5, 15, 30, 60, 120, or more minutes.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such washes can be performed for 5, 15, 30, 60, 120, or more minutes. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$ a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see, *Fundamental Immunology,* Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al. (1990) *Nature,* 348:552–554).

For preparation of monoclonal or polyclonal antibodies, any technique known in the art can be used (see, e.g., Kohler & Milstein (1975) *Nature,* 256:495497; Kozbor et al (1983) *Immunology Today,* 4:72; Cole et al. (1985) pp. 77–96 in *Monoclonal Antibodies and Cancer Therapy*). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al. (1990) *Nature,* 348:552–554; Marks et al. (1992) *Biotechnology,* 10:779–783).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

An "anti-NIK" antibody is an antibody or antibody fragment that specifically binds a polypeptide encoded by a NIK gene, cDNA, or a subsequence thereof.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein For example, polyclonal antibodies raised to a NIK polypeptide from specific species such as rat, mouse, or human can be selected to obtain only those polyclonal antibodies that are specifically immunoreactive with the NIK protein and not with other proteins, except for polymorphic variants and alleles of the NIK protein. This selection may be achieved by subtracting out antibodies that cross-react with NIK molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) binds" to a protein, as defined above.

III. General Recombinant DNA Methods

Numerous applications of the present invention, e.g., identifying NIK genes in mammalian species and making transgenic constructs, involve the cloning, synthesis, maintenance, mutagenesis, and other manipulations of nucleic acid sequences that can be performed using routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers (1981) *Tetrahedron Letts.*, 22:1859–1862, using an automated synthesizer, as described in Van Devanter en al. (1984) *Nucleic Acids Res.*, 12:6159–6168. Purification of oligonucleotides is by either native acrylamide gel electrophoresis or by anion-exchange HPLC as described in Pearson & Reanier (1983) *J. Chrom.*, 255:137–149.

The sequence of the cloned genes and synthetic oligonucleotides can be verified after cloning using, e.g., the chain termination method for sequencing double-stranded templates of Wallace et al. (1 98 1) *Gene*, 16:21–26.

A. Isolating NIK Nucleotide Sequences

In numerous embodiments of the present invention, NIK nucleic acids are isolated and, often, cloned using recombinant methods. Such embodiments are used, e.g., to identify NIK homologs in other mammalian species, as well as during the generation of variants, derivatives, mutants, deletion constructs, expression cassettes, or other sequences derived from NIK, to monitor NIK gene expression, etc.

Often, the nucleic acid sequences encoding NIK proteins and related nucleic acid sequence homologs are cloned from cDNA and genomic DNA libraries by hybridization with probes, or isolated using amplification techniques with oligonucleotide primers. For example, NIK sequences are typically isolated from mammalian nucleic acid (genomic or cDNA) libraries by hybridizing with a nucleic acid probe, e.g. a probe derived from human or mouse NIK (see, e.g., Malinin et al.(1 997) *Nature*, 385:540–544; Song et al. (1997) *PNAS*, 94:9792–9796; U.S. Pat. Nos. 5,843,721, 5,844,073, or 5,854,003; GenBank Accession Nos. NM_016896, AF143094NM_003954, Y10256, AR068515, AR063065, AR062290).

Amplification techniques using primers (e.g., primers comprising nucleotide sequences shown as SEQ ID NOs:1–3) can also be used to amplify and isolate NIK sequences from DNA or RNA (see, e.g., Dieffenbach & Dveksler, *PCR Primer: A Laboratory Manual* (1995)). Primers can be used, e.g., to amplify either the full length sequence or a probe of from one to several hundred nucleotides, which is then used to screen a mammalian library for full-length NIK clones.

Nucleic acids encoding NIK polypeptides can also be isolated from expression libraries using NIK-specific antibodies as probes.

Polymorphic variants, alleles, and interspecies homologs that are substantially identical to a NIK gene can be isolated using NIK nucleic acid probes, and oligonucleotides under stringent hybridization conditions, by screening libraries. Alternatively, expression libraries can be used to clone NIK polymorphic variants, alleles, and interspecies homologs, by detecting expressed homologs immunologically with antisera or purified antibodies made against a NIK polypeptide, which also recognize and selectively bind to the NIK homolog.

More distantly related NIK homologs can be identified using any of a number of well known techniques, including by hybridizing a NIK probe with a genomic or cDNA library using moderately stringent conditions, or under low stringency conditions. Also, a distant homolog can be amplified from a nucleic acid library using degenerate primer sets, i.e., primers that incorporate all possible codons encoding a given amino acid sequence, in particular based on a highly conserved amino acid stretch. Such primers are well known by those of skill, and numerous programs are available, e.g., on the Internet, for degenerate primer design.

Synthetic oligonucleotides can be used to construct recombinant NIK genes for use as probes, for protein expression, or for transgenes to disrupt an endogenous NIK gene. This method is performed using a series of overlapping oligonucleotides usually 40–120 bp in length, representing both the sense and non-sense strands of the gene. These DNA fragments are then annealed, ligated and cloned. Alternatively, amplification techniques can be used with precise primers to amplify a specific subsequence of the NIK nucleic acid. The specific subsequence is then ligated into an appropriate vector.

The nucleic acid comprising a NIK transgene is often cloned into intermediate vectors before transformation into eukaryotic cells for, e.g., integration into the host genome by homologous recombination. These intermediate vectors are typically prokaryote vectors, e.g., plasmids, or shuttle vectors. Vectors, cells, and transfection methods are well known to those of skill and are described, e.g., in Ausubel or in Sambrook, both supra.

In some embodiments, nucleic acids will be used that encode chimeric proteins comprising a NIK polypeptide or domains thereof in combination with a heterologous polypeptide or polypeptides. For example, a domain such as a kinase domain can be covalently linked to a heterologous protein such as a heterologous protein binding domain. Other heterologous proteins of choice include, e.g., luciferase, green fluorescent protein (GFP), and β-gal, each of which is well known in the art B. Detecting NIK Nucleic Acids NIK nucleic acids can be detected, e.g., to detect levels of expression, expression patterns, to identify particular genotypes, etc., using any standard technique.

Typically, NIK polynucleotides will be detected using hybridization-based methods to determine, e.g., NIK RNA levels or to detect particular DNA sequences, e.g., to determine the presence of a particular transgene in a cell. For example, gene expression of NIK can be analyzed by techniques known in the art, e.g., Northern blotting, reverse transcription and amplification of mRNA, dot blotting, in situ hybridization, RNase protection, probing DNA microchip arrays, and the like. In one embodiment, high density oligonucleotide analysis technology (e.g., GeneChip™) is used to identify homologs and polymorphic variants of NIK, or to monitor levels of NIK mRNA.

In certain applications, a NIK DNA sequence will be detected, e.g., to identify the presence or absence of a particular allele, e.g., a wild type or disrupted allele. For example, a NIK allele can be detected in a mammal using Southern blot hybridization, i.e., by isolating genomic DNA, performing a restriction digest on the isolated DNA, separating the restriction fragments electrophoretically, e.g., in an agarose gel, and transferring the separated DNA to a membrane and probing with a specific, labeled sequence. Southern blotting is well known to those of skill, and is taught in numerous sources, including Ausubel et al. and Sambrook et al.

C. Introduction of NIK Transgenes into Cells

Any of the well known procedures for introducing foreign nucleotide sequences into host cells may be used to introduce a vector, e.g., a targeting vector, into cells. These include the use of reagents such as Superfect (Qiagen), liposomes, calcium phosphate transfection, polybrene, protoplast fusion, electroporation, microinjection, plasmid vectors, viral vectors, biolistic particle acceleration (the gene gun), or any of the other well known methods for introducing cloned genomic DNA, cDNA, synthetic DNA or other foreign genetic material into a host cell (see, e.g., Sambrook et al., supra). For the generation of a transgenic cell, it is only necessary that the particular genetic engineering procedure used be capable of successfully introducing at least one transgene into at least one host cell, which can then be selected using standard methods. Methods of culturing prokaryotic or eukaryotic cells are well known and are taught, e.g., in Ausubel et al., Sambrook et al., and in Freshney, *Culture of Animal Cells,* 3d. Ed., (1993), A Wiley-Liss Publication.

IV. Purification of NIK Polypeptides and Immunoassays

Either naturally occurring or recombinant NIK polypeptides can be purified for use in functional assays, binding assays, diagnostic assays, and other applications. Optionally, recombinant NIK polypeptides are purified, e.g., from any suitable bacterial or eukaryotic expression system, e.g., CHO cells or insect cells.

NIK proteins may be purified to substantial purity by standard techniques, including selective precipitation with such substances as ammonium sulfate; column chromatography, immunopurification methods, and others (see, e.g., Scopes (1982) *Protein Purification: Principles and Practice;* U.S. Pat. No. 4,673,641; Ausubel et al., supra; and Sambrook et al., supra).

A number of procedures can be employed when recombinant NIK polypeptide is being purified. For example, proteins having established molecular adhesion properties can be reversibly fused to the NIK polypeptide. With the appropriate ligand, a NIK polypeptide can be selectively adsorbed to a purification column and then freed from the column in a relatively pure form. The fused protein is then removed by enzymatic activity. NIK proteins can also be purified using immunoaffinity columns.

A. Antibodies to NIK Family Members

In numerous embodiments of the present invention, antibodies that specifically bind to NIK polypeptides will be used. Such antibodies have numerous applications, including for the modulation of NIK activity and for immunoassays to detect NIK, and variants, derivatives, fragments, etc. of NIK. Immunoassays can be used to qualitatively or quantitatively analyze the NIK polypeptide. A general overview of the applicable technology can be found in Harlow & Lane, (1988) *Antibodies: A Laboratory Manual.*

Methods of producing polyclonal and monoclonal antibodies that react specifically with NIK polypeptides are known to those of skill in the art (see, e.g., Coligan (1991) *Current Protocols in Immunology*; Harlow & Lane, supra; Goding, *Monoclonal Antibodies: Principles and Practice* (2d ed. 1986); and Kohler & Milstein (1975) *Nature,* 256:495–497). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al. (1989) *Science,* 246:1275–1281; Ward et al. (1989) *Nature,* 341:544–546).

1. Immunological Binding Assays

NIK proteins can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibod-*

*ies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case a NIK protein or an antigenic subsequence thereof). The antibody (e.g., anti-NIK) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled NIK polypeptide or a labeled anti-NIK antibody. Alternatively, the labeling agent may be a third moiety, such a secondary antibody, that specifically binds to the antibody/NIK complex (a secondary antibody is typically specific to antibodies of the species from which the first antibody is derived). Other proteins capable of specifically binding immunoglobulin constant regions, such as protein A or protein G, may also be used as the label agent. These proteins exhibit a strong nonimmunogenic reactivity with immunoglobulin constant regions from a variety of species (see, e.g., Kronval et al. (1973) *J. Immunol*, 111:1401–1406; Akerstrom et al. (1985) *J. Immunol.*, 135:2589–2542). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C. Immunoassays for detecting a NIK protein in a sample may be either. competitive or noncompetitive.

Immunoassays in the competitive binding format can also be used for crossreactivity determinations. For example, a NIK protein can be immobilized to a solid support. Proteins (e.g., NIK proteins and homologs) are added to the assay that compete for binding of the antisera to the immobilized antigen. The ability of the added proteins to compete for binding of the antisera to the immobilized protein is compared to the ability of the NIK polypeptide to compete with itself. The percent cross-reactivity for the above proteins is calculated, using standard calculations. Those antisera with less than 10% cross-reactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of a NIK protein, to the immunogen protein (i.e., NIK protein). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the NIK protein that is required to inhibit 50% of binding, then the second protein is said to specifically bind to the polyclonal antibodies generated to a NIK immunogen.

Polyclonal antibodies that specifically bind to a NIK protein from a particular species can be made by subtracting out cross-reactive antibodies using NIK homologs. For example, antibodies specific to human NIK can be made by subtracting out antibodies that are cross-reactive with mouse NIK. In an analogous fashion, antibodies specific to a particular NIK protein can be obtained in an organism with multiple NIK genes.

The particular label or detectable group used in the assay is not a critical aspect of the invention, as long as it does not significantly interfere with the specific binding of the antibody used in the assay. The detectable group can be any material having a detectable physical or chemical property. Such detectable labels have been well- developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple calorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

V. Transgenic Animals

The present invention provides transgenic and chimeric non-human mammals comprising one or more functionally and structurally disrupted NIK alleles. A "chimeric animal" includes some cells that lack the functional NIK gene of interest and other cells that do not have the inactivated gene. A "transgenic animal," in contrast, is made up of cells that have all incorporated the specific modification which renders the NIK gene inactive or otherwise altered. While a transgenic animal is typically always capable of transmitting the mutant NIK gene to its progeny, the ability of a chimeric animal to transmit the mutation depends upon whether the inactivated gene is present in the animal's germ cells. The modifications that inactivate or otherwise alter the NIK gene can include, for example, insertions, deletions, or substitutions of one or more nucleotides. The modifications can interfere with transcription of the gene itself, with translation and/or stability of the resulting mRNA, or can cause the gene to encode an inactive or otherwise altered NIK polypeptide, e.g., a NIK polypeptide with modified binding properties or kinase activity. In particular, the present transgenic and chimeric animals can lack coding sequences for one or more components of a NIK polypeptide, such as the kinase domain, heterologous protein binding domains, etc. Such transgenes can thus eliminate any one or more codons within an endogenous NIK allele. In a preferred embodiment, a transgenic animal has an allele that lacks at least 20, 30, 40, or more codons of the full-length protein. Further, a transgenic animal can lack non-coding sequences that are required for NIK expression or function, such as 5' or 3' regulatory sequences.

The claimed methods are usefull for producing transgenic and chimeric animals of most vertebrate species. Such species include, but are not limited to, nonhuman mammals, including rodents such as mice and rats, rabbits, ovines such as sheep and goats, porcines such as pigs, and bovines such as cattle and buffalo. Methods of obtaining transgenic animals are described in, for example, Puhler, A., Ed., *Genetic Engineering of Animals*, VCH Publ., 1993; Murphy and Carter, Eds., *Transgenesis Techniques: Principles and Protocols* (*Methods in Molecular Biology*, Vol. 18), 1993; and Pinkert, CA, Ed., *Transgenic Animal Technology: A Laboratory Handbook*, Academic Press, 1994.

In certain embodiments, transgenic mice will be produced as described in Thomas et al. (1999) *Immunol.,* 163:978–84; Kanakaraj et al. (1998) *J. Exp. Med.,* 187:2073–9; or Yeh et al. (1997) *Immunity* 7:715–725.

Typically, a modified NIK gene is introduced, e.g., by homologous recombination, into embryonic stem cells (ES), which are obtained from preimplantation embryos and cultured in vitro. See, e.g., Hooper, ML, *Embryonal Stem Cells: Introducing Planned Changes into the Animal Germline* (Modeem Genetics, v. 1), Int'. Pub. Distrib., Inc., 1993; Bradley et al. (1984) *Nature,* 309, 255–258. Subsequently, the transformed ES cell is combined with a blastocyst from a non-human animal, e.g., a mouse. The ES cells colonize the embryo and in some embryos form the germ line of the resulting chimeric animal. See, Jaenisch (1988) *Science,* 240:1468–1474. Alternatively, ES cells or somatic cells that can reconstitute an organism ("somatic repopulating cells") can be used as a source of nuclei for transplantation into an enucleated fertilized oocyte giving rise to a transgenic mammal. See, e.g., Wilmut et al. (1997) *Nature,* 385: 810–813.

Other methods for obtaining a transgenic or chimeric animal having a mutant NIK gene in its genome is to contact fertilized oocytes with a vector that includes a polynucleotide that encodes a modified, e.g., inactive, NIK polypeptide. In some animals, such as mice, fertilization is typically performed in vivo and fertilized ova are surgically removed. In other animals, particularly bovines, it is preferably to remove ova from live or slaughterhouse animals and fertilize the ova in vitro. See DeBoer et al., WO 91/08216. In vitro fertilization permits the modifications to be introduced into substantially synchronous cells.

Fertilized oocytes are typically cultured in vitro until a pre-implantation embryo is obtained containing about 16–150 cells. The 16–32 cell stage of an embryo is described as a morula, whereas pre-implantation embryos containing more than 32 cells are termed blastocysts. These embryos show the development of a blastocoel cavity, typically at the 64 cell stage. The presence of a desired NIK mutation in the cells of the embryo can be detected by methods known to those of skill in the art, e.g., Southern blotting, PCR, DNA sequencing, or other standard methods. Methods for culturing fertilized oocytes to the preimplantation stage are described, e.g., by Gordon et al. (1984) *Methods Enzymol.,* 101:414; Hogan et al. *Manipulation of the Mouse Embryo: A Laboratory Manual*, C.S.H.L. N.Y. (1986) (mouse embryo); Hammer et al. (1985) *Nature,* 315: 680 (rabbit and porcine embryos); Gandolfi et al. (1987) *J. Reprod. Fert.,* 81:23–28; Rexroad et al. (1988) *J. Anim. Sci.,* 66:947–953 (ovine embryos) and Eyestone et al. (1989) *J. Reprod. Fert.,* 85:715–720; Camous et al. (1984) *J. Reprod. Fert.,* 72:779–785; and Heyman et al. (1987) *Theriogenology,* 27:5968 (bovine embryos). Pre-implantation embryos may also be stored frozen for a period pending implantation.

Pre-implantation embryos are transferred to an appropriate female resulting in the birth of a transgenic or chimeric animal, depending upon the stage of development when the transgene is integrated. Chimeric mammals can be bred to form true germline transgenic animals. Chimeric mice and germline transgenic mice can also be ordered from commercial sources (e.g., Deltagen, San Carlos, Calif.).

Other methods for introducing mutations into mammalian cells or animals include recombinase systems, which can be employed to delete all or a portion of a locus of interest. Examples of recombinase systems include, the cre/lox system of bacteriophage P1 (see, e.g., Gu et al. (1994) *Science,* 265:103–106; Terry et al. (1997) *Transgenic Res.,* 6:349–356) and the FLP/FRT site specific integration system (see, e.g., Dymecki (1996) *Proc. Natl. Acad. Sci. U.S.A.,* 93:6191–6196). In these systems, sites recognized by the particular recombinase are typically introduced into the genome at a position flanking the portion of the gene that is to be deleted. Introduction of the recombinase into the cells then catalyzes recombination which deletes from the genome the polynucleotide sequence that is flanked by the recombination sites. If desired, one can obtain animals in which only certain cell types lack the NIK gene of interest, e.g., by using a tissue specific promoter to drive the expression of the recombinase. See. e.g., Tsien et al. (1996) *Cell.* 87: 1317–26; Brocard et al. (1996) *Proc. Natl. Acad. Sci. U.S.A.,* 93:10887–10890; Wang et al. (1996) *Proc. Natl. Acad. Sci. U.S.A.,* 93:3932–6; Meyers et al. (1998) *Nat. Genet.,* 18:13641).

The presence of any mutation in a NIK gene in a cell or animal can be detected using any method described herein, e.g., Southern blot, PCR, DNA sequencing, or using assays based on any NIK-dependent cell or organismal property or behavior. See, e.g., Ausubel et al., supra.

VI. Modulators and Binding Compounds

As discussed supra, the present invention provides methods for testing the functional effect of a test agent on a transgenic mammal, or on a cell derived from a transgenic mammal, with at least one disrupted NIK allele. In addition, the present invention provides methods for testing the functional effect of a test agent on NIK polypeptides and polynucleotides, and on cells expressing NIK polypeptides and polynucleotides. Such test agents can be any small chemical compound, including polypeptides, polynucleotides, amino acids, nucleotides, carbohydrates, lipids, or any other organic or inorganic molecule. Alternatively, modulators can be genetically altered versions of a NIK gene. Typically, test compounds will be small chemical molecules and peptides. Essentially any chemical compound can be used as a potential modulator or binding compound in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

To identify molecules capable of modulating NIK, e.g., to identify compounds useful in the treatment or prevention of osteoporosis or other NIK-associated diseases and conditions, assays will often be performed to detect the effect of various compounds on NIK activity alone, or on NIK activity or expression in a cell. Such assays can involve the identification of compounds that interact with NIK proteins, either physically or genetically, and can thus rely on any of a number of standard methods to detect physical or genetic interactions between compounds. Such assays can also involve the identification of compounds that affect NIK expression, activity or other properties, such as its phosphorylation or ability to bind other proteins. Such assays can also involve the detection of NIK activity in a cell, either in vitro or in vivo, and can thus involve the detection of, e.g., NF-κB activation using any standard assay, e.g., by measuring NF-κB nuclear localization or the expression of natural or recombinant NF-κB target genes. Such cell-based assays can be performed in any type of cell, e.g., a cell that naturally expresses NIK, or a cultured cell that produces NIK due to recombinant expression.

A. Assays for NIK-Interacting Compounds

In certain embodiments, assays will be performed to identify molecules that physically or genetically interact with NIK proteins. Such molecules may represent molecules that normally interact with NIK to effect, e.g., IL-1 or TNF receptor signal transduction, or may be synthetic or other molecules that are capable of interacting with NIK and that can potentially be used to modulate NIK activity in cells, or used as lead compounds to identify classes of molecules that can interact with and/or modulate NIK. Such assays may represent physical binding assays, such as affinity chromatography, immunoprecipitation, two-hybrid screens, or other binding assays, or may represent genetic assays as described infra.

In any of the binding or functional assays described herein, in vivo or in vitro, any NIK protein, or any derivative, variation, homolog, or fragment of a NIK protein, can be used. In numerous embodiments, a fragment of a NIK protein, e.g., a NIK kinase domain, is used. Such fragments can be used alone, in combination with other NIK fragments, or in combination with sequences from heterologous proteins, e.g., the fragments can be fused to a heterologous polypeptide, thereby forming a chimeric polypeptide.

1. Assays for Physical Interactions

Compounds that interact with NIK proteins can be isolated based on an ability to specifically bind to a NIK protein or fragment thereof. In numerous embodiments, the NIK protein or protein fragment will be attached to a solid support. In one embodiment, affinity columns are made using the NIK polypeptide, and physically-interacting molecules are identified. It will be apparent to one of skill that chromatographic techniques can be performed at any scale and using equipment from many different manufacturers (e.g., Pharmacia Biotech). In addition, molecules that interact with NIK proteins in vivo can be identified by co-immunoprecipitation or other methods, i.e., immunoprecipitation NIK proteins using anti-NIK antibodies from a cell or cell extract, and identifying compounds, e.g., proteins, that are precipitated along with the NIK protein. Such methods are well known to those of skill in the art and are taught, e.g., in Ausubel et al, Sambrook et al., Harlow & Lane, all supra.

Two-hybrid screens can also be used to identify polypeptides that interact in vivo with a NIK polypeptide or a fragment thereof (Fields, et al., *Nature,* 340:245–246 (1989)). Such screens comprise two discrete, modular domains of a transcription factor protein, e.g., a DNA binding domain and a transcriptional activation domain, which are produced in a cell as two separate polypeptides, each of which also comprises one of two potentially binding polypeptides. If the two potentially binding polypeptides in fact interact in vivo, then the DNA binding and the transcriptional activating domain of the transcription factor are united, thereby producing expression of a target gene in the cell. The target gene typically encodes an easily detectable gene product, e.g., β-galactosidase, GFP, or luciferase, which can be detected using standard methods. In the present invention, a NIK polypeptide is fused to one of the two domains of the transcription factor, and the potential NIK-binding polypeptides (e.g., encoded by a cDNA library) are fused to the other domain. Such methods are well known to those of skill in the art, and are taught, e.g., in Ausubel et al., supra.

2. Assays for NIK Protein Activity

NIK genes and their alleles and polymorphic variants encode protein to kinases that promote a variety of cellular and organismal processes, e.g., immune system development, osteoclastogenesis, and others. Accordingly, the activity of NIK polypeptides can be assessed using a variety of in vitro and in vivo assays to determine functional, chemical, and physical effects, e.g., directly measuring the kinase activity of NIK using in vitro kinase assays, measuring the expression or activity of downstream effectors such as NF-κB target genes, measuring the binding of NIK to heterologous proteins, e.g., TRAF1, 2, 3, 5, or 6, or to other molecules (e.g., radioactive binding), measuring NIK protein and/or RNA levels, or measuring other aspects of NIK polypeptides, e.g., phosphorylation levels, transcription levels, and the like. Such assays can be used to test for both activators and inhibitors of NIK proteins. Modulators can also be genetically altered versions of NIK proteins, e.g., dominant negative forms of NIK or of proteins that interact with NIK. Such modulators of activity are useful for, e.g., many diagnostic and therapeutic applications.

The NIK protein of the assay will typically be a recombinant or naturally occurring polypeptide with a sequence as described, e.g., in Malinin et al. (1997) *Nature,* 385:540–544; Song et al. (1997) *PNAS,* 94:9792–9796; U.S. Pat. Nos. 5,843,721, 5,844,073, or U.S. Pat. No. 5,854,003; GenBank Accession Nos. NM_016896, AF143094, NM_003954, Y10256, AR068515, AR063065, or AR062290, or conservatively modified variants thereof Alternatively, the NIK protein of the assay will be derived from a eukaryote and include an amino acid subsequence having amino acid sequence identity to the NIK sequences disclosed any of these references. Generally, the amino acid sequence identity will be at least 60%, optionally at least 70% to 85%, optionally at least 90–95%. Optionally, the polypeptide of the assays will comprise a domain of a NIK protein, such as a kinase domain. In certain embodiments, a domain of a NIK protein, e.g., a kinase domain, is bound to a solid substrate and used, e.g., to isolate any molecules that can bind to and/or modulate their activity. In certain embodiments, a domain of a NIK polypeptide is fused to a heterologous polypeptide, thereby forming a chimeric polypeptide. Such chimeric polypeptides are also useful, e.g., in assays to identify modulators of NIK Samples or assays that are treated with a potential NIK protein inhibitor or activator are compared to control samples without the test compound, to examine the extent of modulation. Control samples (untreated with activators or inhibitors) are assigned a relative NIK activity value of 100. Inhibition of a NIK protein is achieved when the NIK activity value relative to the control is about 90%, optionally 50%, optionally 25-0%. Activation of a NIK protein is achieved when the NIK activity value relative to the control is 110%, optionally 150%, 200–500%, or 1000–2000%.

In another embodiment, transcription levels can be measured to assess the effects of a test compound on NIK signal transduction. A host cell containing a NIK protein of interest is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured using any method known to those of skill in the art to be suitable. For example, mRNA expression of the protein of interest may be detected using Northern blots or by detecting their polypeptide products using immunoassays. Any polynucleotide typically expressed following NIK activation can be used, i.e., any gene with an NF-κB cognate DNA binding site (see. e.g., Lenardo, et al., (1989) *Cell,* 58:227; Grilli, et al. (1993) *Int. Rev. Cytol.,* 143:1; Baeuerle, et al., (994) *Ann. Rev. Immunol.,* 12:141). Such assays can use natural targets of NF-κB or can use reporter genes, e.g., chloramphenicol acetyltransferase, luciferase; β-galactosidase, GFP, and alkaline phosphatase, operably linked to a promoter containing an NF-κB binding site. Furthermore, the protein of interest can be used as an indirect reporter via attachment to a second reporter such as green fluorescent protein (see, e.g., Mistili & Spector (1997) *Nature Biotechnology,* 15:961–964).

The amount of transcription is then compared to the amount of transcription in either the same cell in the absence of the test compound, or it may be compared with the amount of transcription in a substantially identical cell that lacks the protein of interest. A substantially identical cell may be derived from the same cells from which the recombinant cell was prepared but which had not been modified by introduction of heterologous DNA. Any difference in the amount of transcription indicates that the test compound has in some manner altered the activity of the protein of interest.

B. Assessing the Functional Effect of Test Agents on Mammals

In a number of embodiments, the effect of a test agent on a non-human mammal is assessed. For example, the effect of a known NIK-modulating compound can be administered to an animal to assess the NIK-independent effect of the compound on the animal. Such methods are useful, e.g., to detect possible side effects of a candidate NIK-inhibiting drug. In addition, such methods can be used, e.g., to assess the effect of a suspected NIK-modulating compound on NIK activity or expression in vise, or to screen for NIK modulating compounds.

The effects of the test compounds upon the function of any of the herein-described animals can also be measured by examining changes in any physiological process associated NIK activity. For example, one can measure a variety of effects such as changes in bone density, in lymphoid system development, in inflammation of tissues, as indicated by, e.g., pain, heat, redness, swelling, loss of function, dilatation of arterioles, capillaries and venules, with increased permeability and blood flow, exudation of fluids, including plasma proteins and leukocyte migration into the site of inflammation. In addition, any physiological effect can be detected, including any behavioral manifestation, any change in, e.g., temperature, blood pressure, viability, fertility, growth rate, organ function, etc. In addition, any assay or means of assessment described in the Examples, infra, can be used.

C. Combinatorial Libraries

In one preferred embodiment, assessing the effects of a test agent on cells or animals, e.g., transgenic animals with at least one disrupted NIK allele, involve providing a combinatorial chemical or peptide library containing a large number of potential therapeutic compounds (potential modulator or binding compounds). Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.,* 37:487–493 and Houghton, et al. (1991) *Nature,* 354:84–88). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs, et al. (1993) *Proc. Nat. Acad. Sci. U.S.A.,* 90:6909–6913), vinylogous polypeptides (Hagihara, et al. (1992) *J. Amer. Chem. Soc.,* 114:6568), nonpeptidal peptidomimetics with glucose scaffolding (Hirschmann, et al. (1992) *J. Amer. Chem. Soc.,* 114:9217–9218), analogous organic syntheses of small compound libraries (Chen et al., *J. Amer. Chem. Soc.* 116:2661 (1994)), oligocarbiamates (Cho et al. (1993) *Science,* 261:1303), and/or peptidyl phosphonates (Campbell, et al. (1994) *J. Org. Chem.,* 59:658), nucleic acid libraries (see Ausubel, Berger and Sambrook, all supra), peptide nucleic acid libraries (see, e.g., U.S. Pat. No. 5,539,083), antibody libraries (see, e.g., Vaughn, et al. (1996) *Nature Biotechnology,* 14(3):309–314 and PCT/US96/10287), carbohydrate libraries (see, e.g., Liang, et al. (1996) *Science,* 274:1520–1522 and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainir, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

In embodiments involved isolated cells, high throughput assays are preferentially used. In such high throughput assays, it is possible to screen up to several thousand different modulators in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000–20,000 different compounds is possible using the integrated systems of the invention. More recently, microfluidic approaches to reagent manipulation have been developed.

VII. Administration of NIK Modulators

To assess the effect of a test agent on an animal, or to treat or prevent a NIK-associated condition in an animal, administration of a compound can be achieved by any of the routes normally used for introducing a modulator compound into ultimate contact with the tissue to be treated. The modulators are administered in any suitable manner, optionally with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, 17$^{th}$ ed. 1985)).

The NIK modulators, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and nonaqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, intravesically or intrathecally. The formulations of compounds can be presented in unit-dose or multi-dose sealed containers, such as ampules and vials. Solutions and suspensions can be prepared from sterile powders, granules, and tablets of the kind previously described. The modulators can also be administered as part a of prepared food or drug.

The dose administered to a patient, in the context of the present invention is often varied to assess the effect of various concentrations of a compound on a transgenic animal. The dose will also be determined by, e.g., the body weight or surface area of the area to be exposed to the compound. In general, the dose equivalent of a modulator is from about 1 ng/kg to 10 mg/kg for a typical subject. Administration can be accomplished via single or divided doses.

VIII Examples

A. Generation of NIK Knockout Mice

Figure 3:
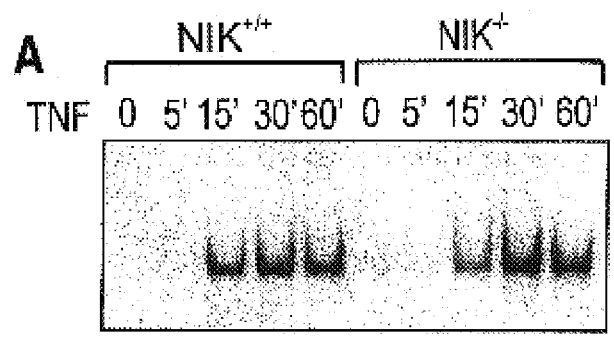
FIG. 3. $NIK^{-/-}$ MEFs display unimpaired signaling and biologic responses to TNF and IL-1. (A, B) Comparable TNF or IL-1 dependent NF-κB activation in mutant or WT cells. $NIK^{-/-}$ or WT MEFs in 6 cm plates were treated with 10 ng/ml of either TNF (A) or IL-1 (B) for the indicated times and NF-κB activation was assessed by EMSA using a probe derived from the Igκ promoter. (C) Development of comparable in vitro kinase activities (KA) of the IKK complex and JNK in cytokine activated cells. $NIK^{--}$ or WT MEFs in 15 cm plates were incubated with or without 50 ng/ml TNF for 10 min. Antibody specific for NEMO (2 µl antiserum) or JNK1 (0.4 µg, Santa Cruz) was added to cell lysates and the kinase activities in immunoprecipitates was assayed using recombinant IκB or c-Jun proteins as substrates. The IKKα, IKKβ and JNK protein levels were assessed by Western blotting (WB) using either a mixture of antibodies specific for IKKα and IKKβ or anti-JNK (D)) $NIK^{-/-}$ maintain sensitivity to TNF dependent cytotoxicity. MEFs ($4 \times 10^4$/well in 96 well plates) from $NIK^{-/-}$, $TRAF2^{-/-}$ or WT mice were incubated with various amounts of INF for 24 hr in the presence of 1 µg/ml cycloheximide. Cell viability was determined by crystal violet staining. (E) Unimpaired cytokine-induced IL-6 production in cells lacking NIK. $NIK^{-/-}$ or WT MEFs ($2 \times 10^4$/well in 96 well plates) were stimulated with various amounts of TNF or IL-1 for 24 hr. IL-6 in the culture supernatant was determined by MTT bioassay using the IL-6 dependent T1165 cell line. (F) Normal TNF or IL-1 induced NO production by $NIK^{-/-}$ cells. $NIK^{-/-}$ or WT MEFs ($2 \times 10^4$/well in 96 well plates) were stimulated with various amounts of TNF or IL-1 for 48 hr in the presence of 250 ng/ml murine IFNγ and the level of nitrite in the supernatants was determined using the Greiss reagent.
Figure 3:
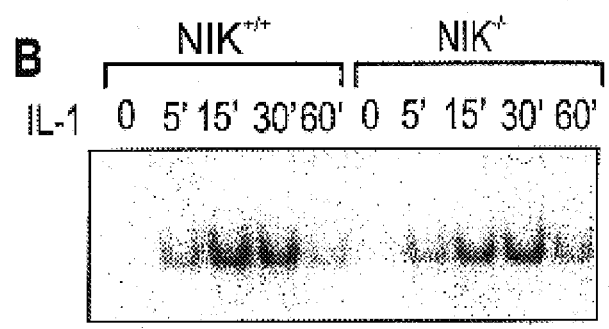
Figure 3:
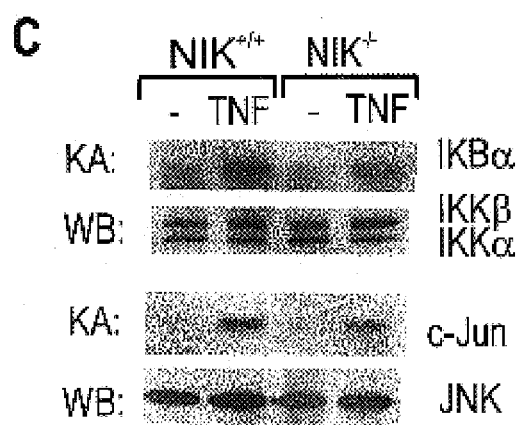

To investigate the role of NIK in NF-κB activation, NIK$^{-/-}$ mice were generated by replacing approximately 1.3 kb of genomic sequence that included the first 40 codons of NIK with a neomycin resistance gene (FIG. 1A). Murine NIK genomic DNA clones were isolated from a 129/SvJ mouse library by using a human NIK cDNA probe. The targeting construct was made by replacing a 1.3 kb fragment containing the first 120 bp of exon 1 with a 1.1 kb neomycin resistance gene cassette in the same orientation as the endogenous NIK. Linearized targeting construct was electroporated into GS-1 ES cells, and G418-resistant clones were selected. Homologous recombinant clones were identified by Southern blot analysis and then injected into C57BL/6 blastocysts. Male chimeric mice were bred to C57BL/6 or 129/Sv/Ev females to generate F1 NIK$^{+/-}$ offspring. Brother and sister matings were carried out to obtain NIK$^{-/-}$ mice. The genotypes of F2 mice or embryos were determined by PCR on ear punch or embryo tissues and verified by Southern blotting. The PCR primers for wild type NIK alleles were 5'-AGTCCAATTCCATGTTGCTGCTGT-3' (NIK7: located in intron 1; SEQ ID NO:1) and 5'-TCTGAGATAGGCATATCCCTGGCT-3' (NIK6: located in intron 1 and deleted in the targeting vector; SEQ ID NO:2). The primers for the disrupted allele were NIK7 and 5'-ATCTTGTTCAATGGCCGATCCCAT-3' (Neo ATG: located in the Neo gene; SEQ ID NO:3). A correctly targeted ES clone was identified by Southern blot analysis and was used to produce chimeric mice that transmitted the mutant allele to their progeny (FIG. 1B). Disruption of the NIK gene was verified by Western blot analysis that revealed the absence of the NIK protein in cells from gene targeted mice (FIG. 1C). Western blotting with anti-IKKα and anti-IKKβ antibodies revealed no differences in the levels of the IKK component proteins in WT and NIK$^{-/-}$ embryonic fibroblasts (MEFs) (FIG. 3C).

B. Phenotypic Effects of NIK Mutation

Figure 2:
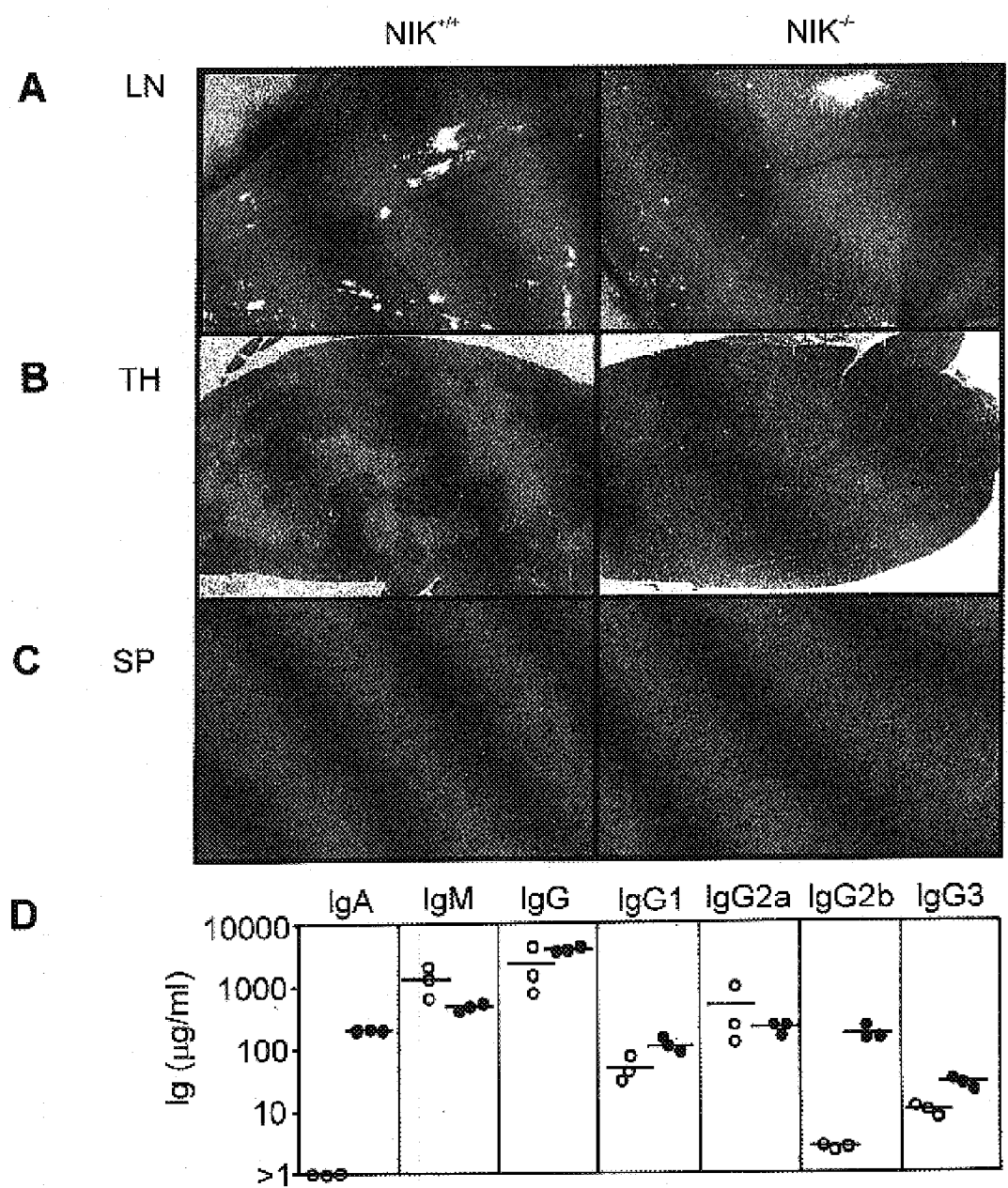
FIG. 2. Abnormal immune system development in $NIK^{-/-}$ mice. (A) Lack of inguinal LN in $NIK^{-/-}$ mice. $NIK^{-/-}$ and WT mice were injected in the hind footpads with 50 µl India ink and inguinal LN were inspected 30 min after injection. Black staining reveals the presence of LN in WT but not gene targeted mice. (B, C) Abnormal lymphoid architecture in $NIK^{-/-}$ mice. H&E staining of thymus (B) or spleen (C) sections from $NIK^{-/-}$ or WT mice (magnification: 10X). (D) Abnormal serum Ig levels in $NIK^{-/-}$ mice. Serum Ig levels of WT mice (closed circle) and $NIK^{-/-}$ mice (open circle) were measured by ELISA and concentrations calculated based on mouse Ig standards.

NIK$^{-/-}$ mice are born in Mendelian proportions (22.4% out of 410 mice born), are healthy and show no differences in growth, behavior, reproductive ability or capacity to nurse compared to WT mice. However, NIK$^{-/-}$ mice display abnormal lymphorganogenesis. They lack all peripheral lymph nodes (LN), including cervical, inguinal, mesenteric, popliteal, and axillary LNs (FIG. 2A) and do not form Peyer's patches. Moreover the thymus and spleen of 6–8 week old NIK$^{-/-}$ mice display a disrupted lymphoid architecture as revealed by hemotoxylin and eosin staining. The thymus lacks a clear distinction between the cortical and medullary regions and the total medullary area is reduced (FIG. 2B). The spleen has a disorganized white pulp, a red pulp that is invaded by leukocytes and shows no evidence of marginal sinus and follicle organization (FIG. 2C). Yet despite the abnormal lymphoid architecture, T and B cell development in the gene-targeted mice are relatively normal. Thymi and spleens of HIK$^{-/-}$ and WT mice show similar cellularity. In addition, FACS analysis of lymphocytes derived from these two organs revealed the presence of all T and B cell lineages although subtle quantitative differences among the component populations could be observed. Splenic monocytes and neutrophils were present in undiminished amounts. In unmanipulated mice, the absence of NIK leads to undetectable levels of serum IgA and a 65-fold reduction of IgG2b. The levels of all other immunoglobulin subclasses in the serum of HIK$^{-/-}$ mice are within 3 fold of that observed in WT mice (FIG. 2D). Thus NIK$^{-/-}$ mice display a clear defect in lymphoid system development.

To assess whether NIK was required for TNF- or IL-1-induced signaling, NIK$^{-/-}$ or WT MEFs were treated with either ligand for various periods of time. No differences were observed between the two cell types (FIGS. 3A and 3B). Similar responses were also obtained when NF-κB activation kinetics were monitored in bone marrow derived macrophages (BMM) or when cells were treated with different doses of TNF or IL-1 for a fixed 30 min incubation period. As expected from the aforementioned results, TNF or IL-1 also activated the IKK complex and INK in NIK$^{-/-}$ MEFs (FIG. 3C, IL-1 data not shown). Thus NIK is not required for TNF- or IL-1-induced activation of NF-κB DNA binding activity.

To investigate whether NIK is involved in other aspects of TNF and IL-1 signaling, induction of three different biologic responses in NIK$^{-/-}$ cells was monitored. First, the sensitivity of NIK$^{-/-}$ and WT MEFs to TNF-induced apoptosis was compared. No differences were observed when the cells were incubated with various doses of cytokine in the presence of cycloheximide. In contrast, MEFs lacking TRAF2, a TNF signal transducer, display enhanced sensitivity to TNF-mediated killing as previously described (Yeh, W., et al. (1997) *Immunity*, 7:715) (FIG. 3D). Second, no differences were observed in IL-6 production by NIK$^{-/-}$ and WT MEFs treated with different doses of TNF or IL-1 (FIG. 3E). Third, NIK$^{-/-}$ and WT MEFs produced comparable amounts of nitric oxide (NO) when exposed to different doses of TNF or IL-1 in the presence of IFNγ (FIG. 3F). Thus, like the results obtained by monitoring NF-κB activation, no obligate role for NIK was detected in several TNF- or IL-1-induced cellular responses.

Figure 4:
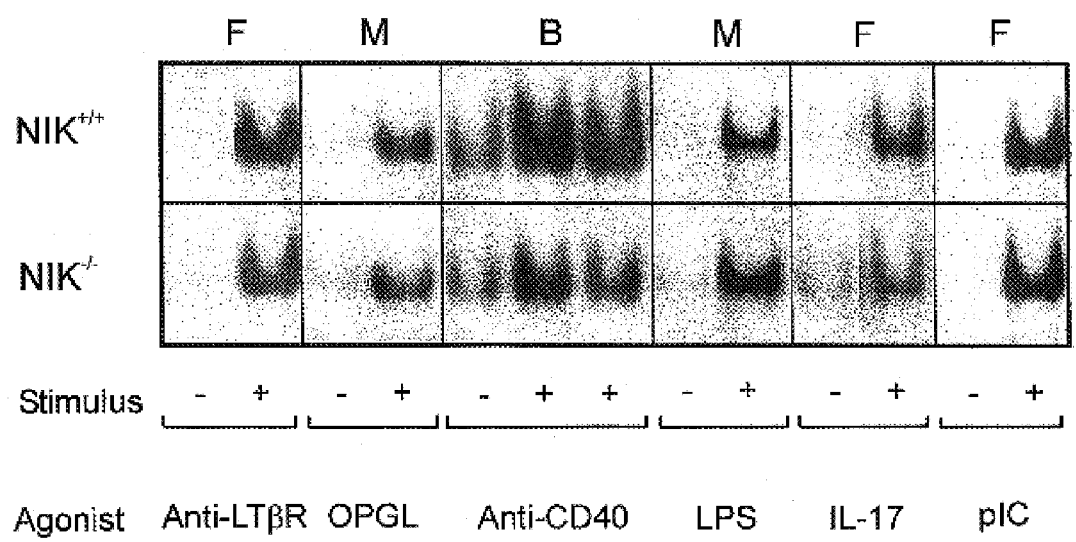
FIG. 4. NF-κB activation occurs in $NIK^{-/-}$ cells following stimulation with a variety of different agonists. Primary $NIK^{-/-}$ or WT fibroblasts (F), B cells (B) or Bone Marrow-derived Macrophages (BMM) (M) were stimulated with LTβR specific mAb (1 µg/ml; 1 hr), OPGL (100 ng/ml; 15 min), anti-CD40 antibody (10 µg/ml; 1 and 4 hr), LPS (10 µg/ml; 1 hr), IL-17 (100 ng/ml; 30 min), pIC (100 µg/ml; 2 hr). NF-κB activation was assessed by EMSA as in FIGS. 3A/B.

To investigate the possibility that NIK plays an essential role in effecting NF-κB activation induced by other cytokines or microbial products, NF-κB activation was monitored in MEFs, BMM or B cells following treatment with LTβR- or CD40-specific antibodies, OPGL, IL-17, LPS or double stranded RNA (poly [rI]: poly [rC], pIC). In all cases except anti-CD40 treatment, NF-κB activation was identical between NIK$^{-/-}$ and WT cells (FIG. 4). In contrast, purified NIK$^{-/-}$ B cells manifested 2 fold less activated NF-κB following CD40 stimulation that was also more transient compared to that induced in purified WT B cells. Thus, NIK is not obligatorily required for NF-κB activation mediated by a wide variety of different receptors but may contribute to the magnitude of the signaling response in certain cell types such as B cells.

Figure 5:
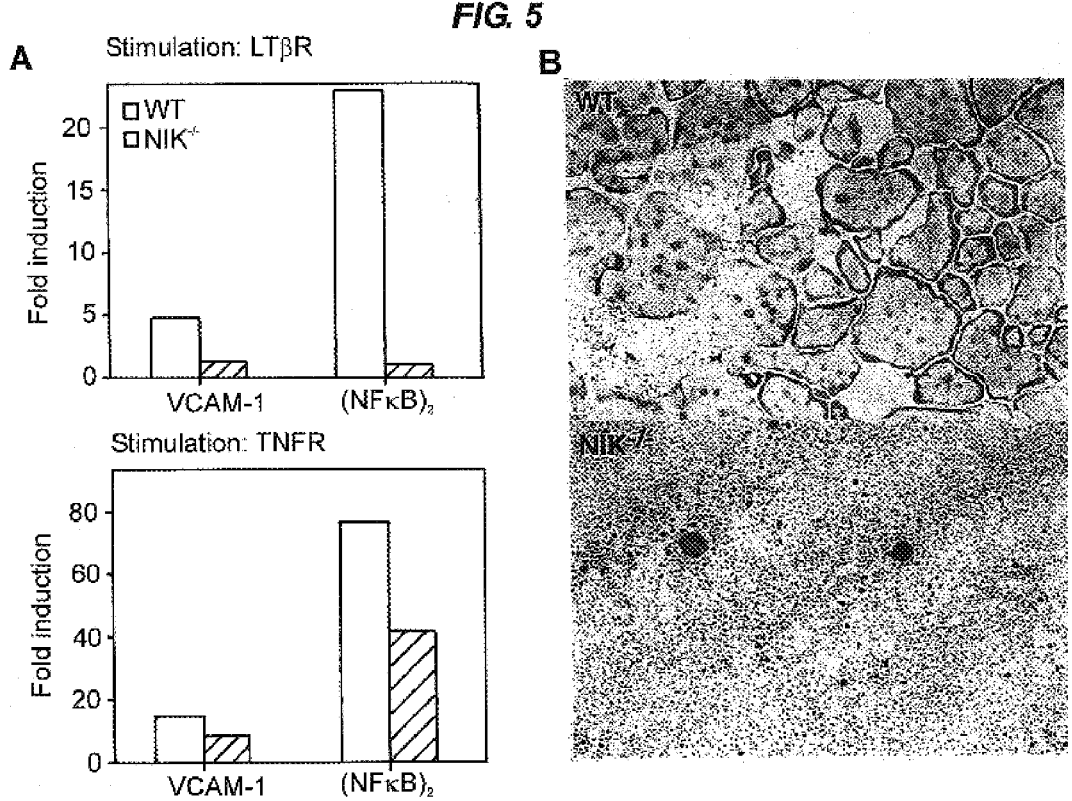
FIG. 5. Defective in vitro cellular responses induced by anti-LTβR or OPGL in $NIK^{-/-}$ cells. (A) Immortalized MEFs ($10^5$/well in 6 well plates) were transiently transfected using the SuperFect reagent (Qiagen) with 2 µg of p288VCAM-Luc (Iademarco, M., et al. (1992) *J. Biol. Chem.*, 267:16323) or (NE-κB)$_2$-Luc (containing 2 synthetic NF-κB sites derived from IFN-β (Liou, H., et al. (1994) *Mol. Cell Biol.*, 14:5349)), together with 1 µg pRL-TX (Promega) for transfection normalization. After overnight incubation, the cells were stimulated with anti-LTβR (1 µ/ml) or TNF (10 ng/ml) for 6–8 hrs, and luciferase activity was determined. Data are presented as the fold induction of luciferase activity over the unstimulated control.

It was also determined whether NIK was required for induction of cellular responses to ligands other than TNF and IL-1. The lymphoid system defect in NIK$^{-/-}$ mice is similar (but not identical) to that observed in LT- or OPGL-deficient mice and in mice that lack a combination of p50 and p52 Rel family members (De Togni, P., et al. (1994) *Science*, 264:703; Koni, P., et al. (1997) *Immunity*, 6:491; Kong, Y., et al. (1999) *Nature*, 397:315; Franzoso, G., et al. (1997) *Genes Dev.*, 11:3482). To assess cellular responsiveness to LTβ, NIK$^{-/-}$ or WT MEFs were transiently transfected with two different luciferase reporter constructs driven by NF-κB regulated promoters and then stimulated with either anti-LTβR or TNF. Whereas in WT cells, anti-LTβR induced a 4 and 19.6 fold increase in luciferase expression driven by VCAM-1- and (NF-κB)$_2$-promoters, respectively, no induction was observed in NIK$^{-/-}$ MEFs (1.1 and 1.0 fold induction, respectively) (FIG. 5A). The activation of both reporter constructs was only partially reduced in NIK$^{-/-}$ MEFs stimulated with TNF. Thus despite the fact that anti-LTβR receptor was capable of inducing NF-κB activation in NIK$^{-/-}$ cells as evidenced by measuring expression of DNA binding activity, it failed to promote transcriptional activation in these cells of two NF-κB-responsive promoter sequences. To assess cellular responses induced by OPGL, BMM derived from WT or NIK$^{-/-}$ mice were cultured in the presence of this cytokine and osteoclastogenesis. was determined. BMM derived from WT mice vigorously differentiated into large multinucleated TRAP-positive osteoclasts following culture with OPGL. In contrast, osteoclastogenesis was strikingly absent when NIK$^{-/-}$ BMM were used in the assay (FIG. 5B).

It is notable that there are significant differences between NIK$^{-/-}$ mice and mice lacking either OPGL or its receptor (RANK) with respect to osteoclastogenesis in vivo (Kong, Y., et al. (1999) *Nature*, 397:315; Dougall, W., et al. (1999) *Genes Dev.*, 13:2412; Li, J., et al. (2000) *Proc. Natl. Acad. Sci. U.S.A.*, 97:1566). Whereas mice lacking OPGL or RANK have frank abnormalities in osteoclastogenesis and become osteopetrotic at an early age, young NIK$^{-/-}$ mice (5–6 weeks) have normal numbers of osteoclasts and do not show bone abnormalities (data not shown). Thus, factors in vivo compensate for the failure of isolated NIK$^{-/-}$ BMMs to undergo osteoclastogenesis in vitro. These factors must be absent in mice lacking OPGL. On the other hand, osteociastogenesis induced by parathyroid hormone is suppressed in the NIK$^{-/-}$ mouse. Thus, NIK appears essential for stimulated osteoclast recruitment.

Importantly, NIK$^{-/-}$ mice and aly/aly mice share many of the same deficits. Both show indistinguishable lymphoid system abnormalities including the disrupted thymic architecture that is not seen in any other mice that lack other members of the TNF/LT or TNFR families (Koni, P., et al. (1997) *Immunity*, 6:491; Eugster, H., et al. (1996) *Int. Immunol.*, 8:23; Koni, P., et al. (1998) *J. Exp. Med.*, 187:1977; Peschon, J., et al. (1998) *J. Immunol.*, 160:943; Futterer, A., et al. (1998) *Immunity*, 9:59). In addition, both types of mice lack IgA, which is most likely attributable to the absence of Peyer's patches in these mice. However, there are subtle differences between the gene-targeted mice and those harboring the natural mutation. Specifically, compared to aly/aly mice, NIK$^{-/-}$ mice exhibit a milder phenotype with respect to IgG and IgM levels (which are only moderately different than those in WT mice) and show no deficit in the capacity to nurse their young (Miyawaki, S., et al. (1994) *Eur. J. Immunol*, 24:429). More importantly, NIK$^{-/-}$ cells can activate NF-κB following treatment with anti-CD40 (although 2-fold less than seen in WT cells) while a recent report using B cells derived from aly/aly mice shows a major deficit in CD40-mediated signaling (Garceau, N., et al., (2000) *J Exp Med*, 191:381). It is thus possible that the presence of the abnormal NIK protein in the aly/aly mouse is contributing in either a positive or negative manner to the phenotype that this mouse exhibits.

These results suggest that NIK plays a critical role in the development of certain functional cellular responses and thus may act either downstream of the NF-κB activation step or independent of it. The current study leaves unanswered the nature of the integrating signal in cytokine-induced NF-κB activation response. It is possible that an unknown kinase yet to be discovered is required for TNF receptor signaling or that NIK is redundant with other kinases capable of activating IKK. Possible candidates for the latter are the MEKKs. MEKK1, for example can activate IKK and NF-κB in vitro (Nemoto, S., et al. (1998) *Mol. Cell. Biol.*, 18:7336; Lee, F., et al. (1998) *Proc. Natl. Acad. Sci. U.S.A.*, 95:9319). Finally, it is possible that the ligand assembled, activated TNF receptor complex may directly activate IKK eliminating a need for an intermediate kinase such as NIK. More work is needed to define the molecular events that result in IKK activation and to define NIK's physiologic function. Clearly these investigations will be facilitated by the availability of the NIK$^{-/-}$ mouse.

SEQ ID NO;3 primer specific for the disrupted allele, located within the NEO gene

ATCTTGTTCAATGGCCGATCCCAT

SEQUENCE LISTING

```
<160> NUMBER OF SEQ ID NOS: 3

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence:NIK7 PCR
      primer for wild type NF-kappaB inducing kinase (NIK)
      allele, located in intron 1

<400> SEQUENCE: 1
agtccaattc catgttgctg ctgt                                          24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:NIK6 PCR
      primer for wild type NF-kappaB inducing kinase (NIK)
      allele, located in intron 1 and deleted in
      targeting vector

<400> SEQUENCE: 2
tctgagatag gcatatccct ggct                                          24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:Neo ATG PCR
      primer specific for disrupted NF-kappaB inducing
      kinase (NIK) allele, located wihin Neo gene

<400> SEQUENCE: 3
atcttgttca atggccgatc ccat                                          24
```

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

SEQUENCE LISTING
Primers for Wild Type Allele
SEQ ID NO:1
  NIK7 primer, located in intron 1 of NIK
  AGTCCAATTCCATGTTGCTGCTGT
SEQ ID NO:2
  NIK6 primer, located in intron 1 of NIK
  TCTGAGATAGGCATATCCCTGGCT

What is claimed is:

1. A transgenic mouse comprising a homozygous disruption of the NIK gene, wherein said NIK gene is disrupted by insertion of a transgene within a NIK locus within the genome of said mouse, wherein no NIK protein is expressed, and said mouse exhibits a phenotype comprising abnormal immune system development.

2. The mouse of claim 1, wherein said phenotype is selected from the group consisting of impaired lymph node development, absence of Peyer's Patches, disupted lymphoid architecture, decreased IgA levels, decreased IgG2b levels, or impaired NFkB activation in response to OPGL.

3. The mouse of claim 1, wherein said transgene is inserted into said NIK locus by homologous recombination, and wherein said insertion removes at least a portion of an endogenous NIK gene within the genome of said mouse, said portion comprising at least 1 kb, and including at least 40 codons, of said endogenous NIK gene.

4. The mouse of claim 3, wherein said insertion of said transgene results in the replacement of said portion of said endogenous NIK gene with a nucleic acid sequence encoding a selectable marker.

5. The mouse of claim 4, wherein said selectable marker is a neomycin resistance gene.

6. A cell isolated from the transgenic mouse of claim 1.

7. A method of making a transgenic mouse comprising a homozygous disruption of the NIK gene, said method comprising:
   (i) transfecting a plurality of mouse embryonic stem cells with a nucleic acid comprising a NIK gene that is disrupted by insertion of a selectable marker;
   (ii) selecting for transgenic embryonic stem cells that have incorporated said nucleic acid into their genome;
   (iii) introducing at least one of said transgenic embryonic stem cells into an embryo to produce a chimeric mouse comprising at least one of said transgenic embryonic stem cells;
   (iv) breeding said chimeric mouse with a wild type mouse to obtain F1 progeny that are heterozygous for a disrupted NIK gene; and
   (v) breeding a male mouse of said F1 progeny with a female mouse of said F1 progeny to obtain F2 progeny that are homozygous for said disrupted NIK gene; wherein said mouse comprises a homozygous disruption of the NIK gene, wherein no NIK protein is expressed, and further exhibits a phenotype comprising abnormal immune system development.

* * * * *

UNITED STATES PATENT AND TRADEMARK OFFICE
CERTIFICATE OF CORRECTION

PATENT NO.    : 6,822,138 B1
DATED         : November 23, 2004
INVENTOR(S)   : Robert D. Schreiber et al.

It is certified that error appears in the above-identified patent and that said Letters Patent is hereby corrected as shown below:

<u>Title page,</u>
Item [75], Inventors, please add the following inventors to the patent:
-- Lin Wu
Li Yin Drake
Deborah Veis Novack --

Signed and Sealed this

Fifteenth Day of March, 2005

JON W. DUDAS
*Director of the United States Patent and Trademark Office*